United States Patent [19]
Morrissey

[11] Patent Number: 5,614,671
[45] Date of Patent: *Mar. 25, 1997

[54] HUMIDITY SENSING APPARATUS AND METHOD

[75] Inventor: James F. Morrissey, Norwood, Mass.

[73] Assignee: The United States of America as represented by the Secretary of the Air Force, Washington, D.C.

[ * ] Notice: The term of this patent shall not extend beyond the expiration date of Pat. No. 5,365,784.

[21] Appl. No.: 229,489

[22] Filed: Apr. 18, 1994

Related U.S. Application Data

[63] Continuation of Ser. No. 876,836, Apr. 30, 1992, Pat. No. 5,365,784.

[51] Int. Cl.$^6$ .............................. G01N 27/04; G01W 1/00
[52] U.S. Cl. ........................................................ 73/335.05
[58] Field of Search ............................ 73/29.02, 335.02, 73/335.05, 29.05, 170.28

[56] References Cited

U.S. PATENT DOCUMENTS

| | | | |
|---|---|---|---|
| 2,352,578 | 6/1944 | Wallace | 73/170.28 X |
| 3,599,862 | 8/1971 | Hogan et al. | 73/335.03 X |
| 4,227,411 | 10/1980 | Abramovich | 73/335.02 |
| 4,793,181 | 12/1988 | Djorup | 73/335.02 |
| 4,793,182 | 12/1988 | Djorup | 73/335.02 |
| 5,365,784 | 11/1994 | Morrissey | 73/335.05 X |

Primary Examiner—Michael Brock
Attorney, Agent, or Firm—Stanton E. Collier

[57] ABSTRACT

The present invention is a humidity sensor which can be used in a radiosonde. The humidity sensor includes a heat sink attached to the radiosonde, a Peltier cooler attached to the heat sink, a carbon element with a thermistor attached therein or thereon, and a control means. The resistance of the carbon element is adjusted to a predetermined level to maintain a relative humidity of about 33, in particular. The control means monitors this resistance and adjusts the Peltier cooler accordingly. The thermistor responding to the temperature of the carbon element outputs a resistance indicative of the temperature on the sensor surface.

10 Claims, 7 Drawing Sheets

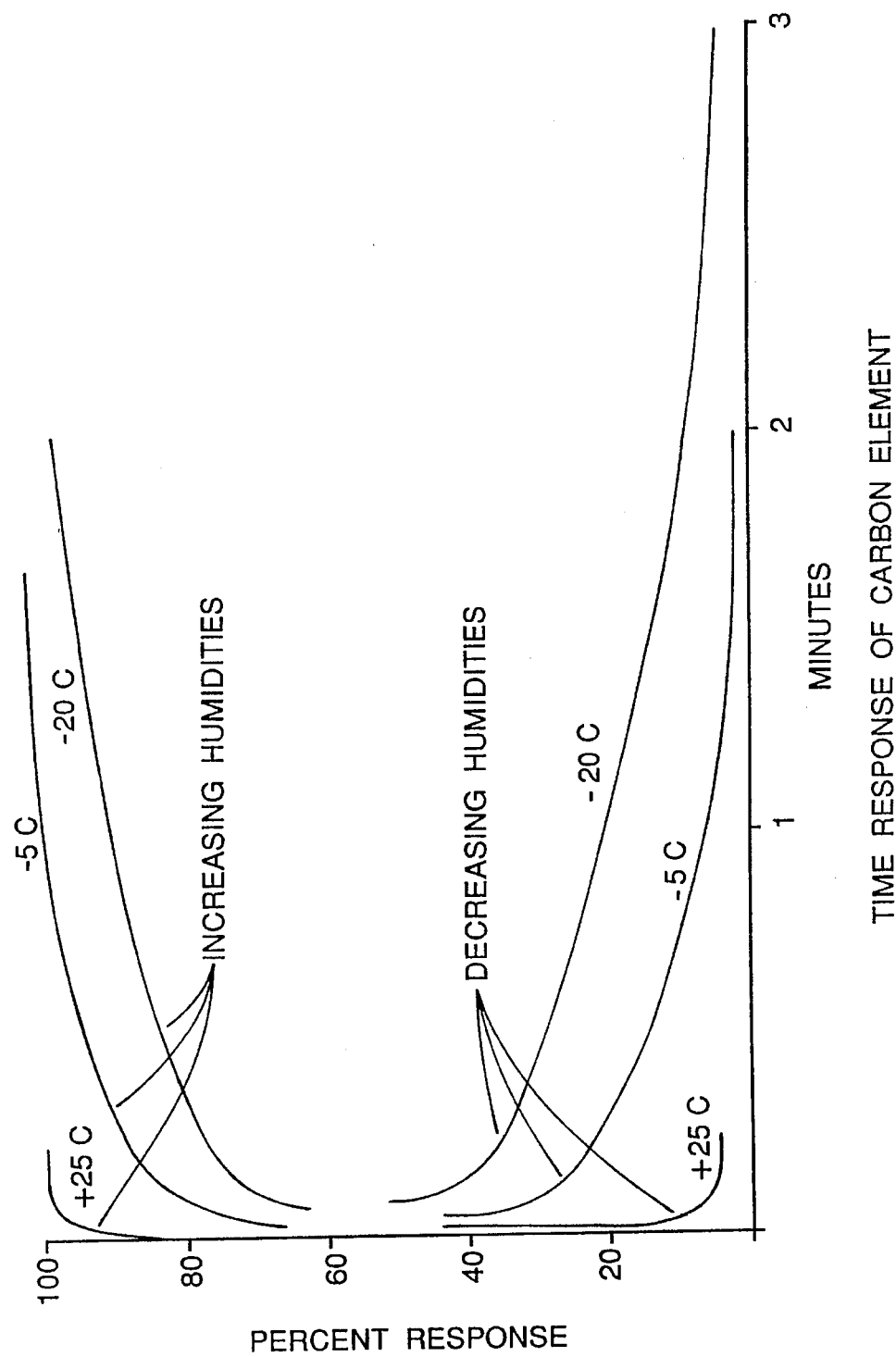

HUMIDITY SENSING APPARATUS AND METHOD

STATEMENT OF GOVERNMENT INTEREST

The invention described herein may be manufactured and used by or for the Government for governmental purposes without the payment of any royalty thereon.

This application is a continuation of application Ser. No. 07/876,836, filed 30 Apr. 1992, now U.S. Pat. No. 5,365,784.

BACKGROUND OF THE INVENTION

The present invention relates to atmospheric sciences, and, in particular, relates to an apparatus and a method of determining dew point temperature and/or water vapor pressure, for example.

Radiosonde humidity measurements are routinely made with transducers which respond to the relative humidity of the air, i.e., carbon element, humicap sensor, lithium chloride, hair, goldbeaters skin. All are designed to provide a variation in some electrical quantity such as resistance or capacitance or impedance with changes in relative humidity. The value of this electrical property is then sensed and telemetered to the ground where it is used to compute the relative humidity. All of these devices exhibit some temperature dependency, that is the relationship of the electrical quantity used to relative humidity is not one curve, but a family of curves, one for each temperature.

The most commonly used sensor in the United States is the carbon element. In radiosonde applications the carbon element is located in a duct which serves the dual purpose of shielding the element from rain and from insolation. Since the carbon element responds to relative humidity (RH), it is necessary to know the temperature of the air to calculate other measures of humidity, e.g., water vapor pressure, dew/frost point temperature, specific humidity, absolute humidity and mixing ratio. In some of these, the pressure of the air is also required for calculation. In attempting to measure the relative humidity of the air, the defining temperature is the temperature of the surface of the sensor which thermodynamic considerations dictate to be identical with the air temperature immediately in contact with the sensor. This surface temperature is in general distinct from the free air temperature, i.e., the temperature of the air before it comes in contact with any part of the radiosonde or the sensor itself. In addition, any error in determining the free air temperature can introduce error in the humidity terms computed from the relative humidity measurement.

The most basic and the largest source of error in the radiosonde carbon humidity type of measurement is caused by the temperature difference between the surface of the carbon element and the free air temperature. When a parcel of air comes in contact with the sensor the temperature of the parcel is changed from its free air value to the sensor surface value. This results in the relative humidity of that parcel being changed and it is this modified value of relative humidity which is then sensed by the carbon element. This error results in related errors in any of the other measures of humidity calculated using this value.

Besides the temperature effects there are two other characteristics which result in significant errors: the element has poor sensitivity at low relative humidities (RH<25%) and its response time characteristic degrades markedly at low temperatures. Because of the low sensitivity at low RH, it is standard practice not to report humidities below 20% RH on synoptic radiosondes. Because of the response time degradation, the depiction of humidity featureas with vertical scales of less than 400 m will be very limited at temperatures of −20° C. or lower. All three of the error producing characteristics can severely affect the measurement accuracy at any altitude but their combined influence is most often felt at higher altitudes (>4 km).

The following patents are incorporated by reference as to their teachings on humidity detection, etc.: U.S. Pat. Nos. 4,911,357; 4,801,211; 4,080,564; 4,793,182; and 4,793,181.

In recent years there has been an increasing requirement for more accurate humidity measurements. These requirements come from satellite applications that require improved humidity data both to calibrate and to validate their systems performance for new atmospheric models that are sensitive to middle and upper troposphere moisture, and from military applications with the increased emphasis on electro-optical systems. Not only is there an increased need for accuracy in general but many of the new requirements are for increased accuracy at the higher altitudes where the current measurements are most deficient.

SUMMARY OF THE INVENTION

The present invention provides a humidity sensing apparatus and a process to use such. The humidity sensing apparatus includes a humidity sensor which has a heat sink, a Peltier cooler on the top thereof, a carbon element sensor with a thermistor embedded or attached therein and this is placed on top of the Peltier cooler.

The resistance of the carbon element is used as the control element in a feedback loop designed to control the relative humidity the carbon element measures by controlling the temperature of the element. In the preferred mode of operation the control circuit would maintain the element temperature so the relative humidity would stay constant at a value of about 33% RH. At this point the resistance of the carbon element is invariant with temperature so that the control circuit can be designed to maintain the resistance of the carbon element at a constant value. The temperature of the carbon element is then measured by the embedded or attached thermistor and this temperature is used to calculate the water vapor pressure of the air. This device is a water vapor pressure measuring device which can be directly converted to dew/frost point information without knowledge of the ambient temperature. In order to operate at a constant relative humidity other than 33%, an additional feedback from the embedded or attached thermistor would be required to compensate for temperature effects in the carbon element.

Therefore, one object of the present invention is to provide a humidity sensor that minimizes errors due to sensor surface temperature, low sensitivity at low humidity, and long response time at low air temperatures.

Another object of the present invention is to provide a humidity sensor that operates at a constant value of relative humidity of about 33% relative humidity.

Another object of the present invention is to provide a humidity sensor that maintains the carbon element resistance at a constant value to increase the response time to humidity changes.

Another object of the present invention is to provide a humidity sensor having a temperature feedback for operating at any humidity.

These and many other objects and advantages of the present invention will be readily apparent to one skilled in the pertinent art from the following detailed description of preferred embodiments of the invention and the related drawings.

BRIEF DESCRIPTION OF THE DRAWINGS

FIG. 7 illustrates humidity response of the carbon element at various temperatures.

DETAILED DESCRIPTION OF THE PREFERRED EMBODIMENT

The carbon humidity element used in U.S. radiosondes was developed in the 1950s. Since that time its manufacturing process has not been tightly controlled in that, for the most part, it has been procured by a performance specification. Indeed, the element in use today exhibits much less hysteresis and is made with a different type of carbon due to environmental considerations. Nevertheless, the general principal of operation is the same. The carbon type humidity element consists of a humidity-sensitive film which is deposited by a spraying or dipping process on a base plate substrate. The electrical resistivity of the film varies with the humidity of the sensed environment thus providing an electrical transducer for the measurement of water vapor in the atmosphere.

Figure 1:
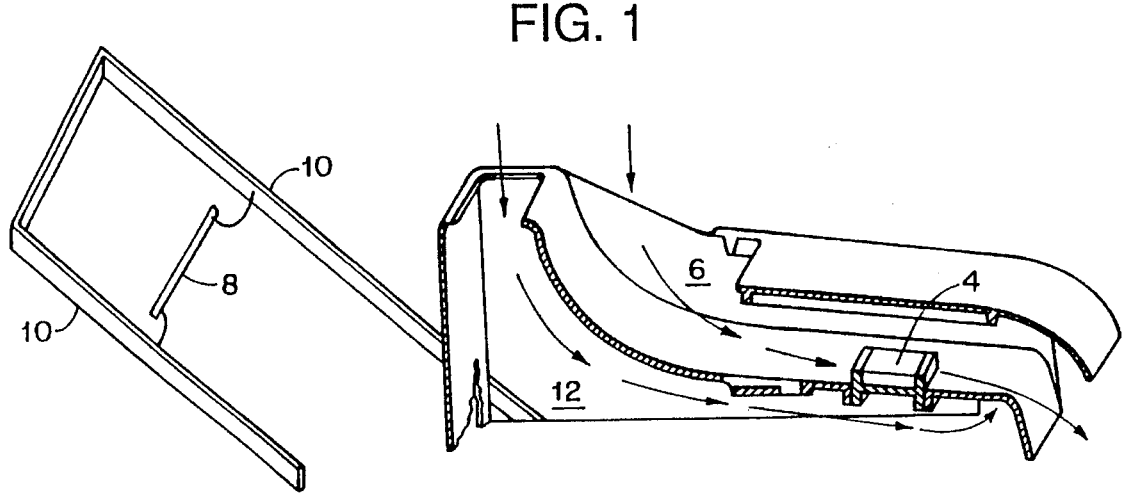
FIG. 1 illustrates a partial view of the air ducts and sensors in a radiosonde.

In FIG. 1, in radiosonde applications the conventional carbon element 4 is located in a duct 6 which serves the dual purpose of shielding the element 4 from rain and from insolation. Since the carbon element 4 responds to relative humidity, knowledge of the air temperature is necessary to compute any of the other common measures of humidity, e.g., vapor pressure, dew/frost point, absolute humidity. In radiosonde applications the air temperature is measured using a thermistor 8 which is located outside the radiosonde and supported by arms 10. The current shape of the duct 6 was the result of work of Morrissey and Brousaides. This work quantified the magnitude of the temperature induced errors using the earlier ducts. The principal differences between the old and new ducts are an extended curved exit, blackening of the inside walls and a secondary air path 12 beneath the duct 6. While this duct reduced the errors due to insolation it did not eliminate them and did not treat other temperature effects such as lag. This duct resulted in errors of about 10% of the measured value due to insolation effects above 500 mb. A similar temperature induced error above 500 mb of about 8% of the measured value is due to the thermal lag of the element and usually has the same sense as the insolation error in the troposphere.

As noted above since the carbon element 4 responds to relative humidity it is necessary to know the air temperature to determine any absolute measure of humidity. More specifically the surface temperature of the carbon film on the substrate itself is the defining temperature since heat transfer considerations dictate this to be the same as the air immediately in contact with the surface. There are three temperatures important to this measurement: the free air temperature, the surface temperature of the film, and the air temperature as measured by the thermistor 8. Any differences between these temperatures introduce error in the humidity measurement. The magnitude of humidity error due to temperature differences between the carbon element 4 and the air is given in Table 1 where it is broken into components, insolation effect and thermal lag effect.

TABLE 1

| | Residual Temperature Induced Errors in Daytime Humidity Measurements | |
|---|---|---|
| Layer, mbar | Insolation Error (% of Measured Valve) | Thermal Lag Error (% of Measured Value) |
| 1013–701 | 3% | 3% |
| 700–501 | 6% | 4% |
| 500–351 | 9% | 6% |
| 350–250 | 14% | 9% |

The magnitude of error caused by temperature differences between the thermistor 8 and the air is less than the insolation and lag effects and, during the day; of the opposite sense. For example, at 5 km the temperature of the thermistor would be about 0.3° C. above the air temperature resulting in about a 2% error in any absolute humidity calculation.

The low sensitivity at low RH problem will be totally eliminated by the present invention in that the element will never experience low RH values but will be maintained at 33% RH at all times. In fact low RH values should be one of the most accurate areas. For example, if the element can be maintained within 1% RH of 33% RH then if the RH of the fee air is 5% the error in measuring this should be less than 0.5% RH. It should be noted that the same effect that causes the high accuracy at low RH will cause a loss of accuracy at high RH. If, as above, the element can be kept within 1% RH at 33% RH, this would result in a 3% RH uncertainty for an ambient of 100% RH. This would still be an improvement on current measurements since the insolation, thermal lag, and humidity response effects will be greatly reduced.

The response of the element to change in humidity is not that of a simple first order system. Earlier researchers, Marchgraber and Kobayashi, attributed this to there being a relatively fast "surface" effect and a slower volume or bulk effect. In addition the response gets markedly longer at lower temperatures. (FIG. 7)

The problem of increasingly long response times at low temperatures should also be eliminated for the most part. First the fact that it will be part of an active servo loop will allow designing a faster response. In addition there are physical properties of the sensor that will collaborate with the servo loop to improve the response. By designing around 33% RH the system only has to maintain a constant carbon element resistance. The fact that at 33% RH the resistance of the carbon element remains constant at all temperatures indicates that the amount of water in and on the sensor is invariant with temperature at 33% RH. This indicates that even though the RH of the free air changes there is no net mass transfer to the sensor when it goes from one equilibrium state to another. This will allow the servo loop to react to the surface effects and return the sensor to equilibrium before any significant volume effects occur. Data indicate that even at −20° C. more than 20% of the response to a step function change occurs in less than one second. Consequently if the Peltier cooler has sufficient capacity, a 90% response to a negative step function at −20° C. in less than 5 seconds is to be expected whereas the current sensor takes about 2 minutes for a 90% response at the same temperature.

If absolute humidity is required, the value of air temperature is needed to compute it but the computation is much less sensitive to errors in the measurement of the air temperature. Whereas a temperature measurement error of 0.3° C. was found to cause a 2% error in absolute humidity in the old system, a 0.3° C. error in air temperature measurement for the present invention results in less than 0.2% error in absolute humidity.

Figure 2A:
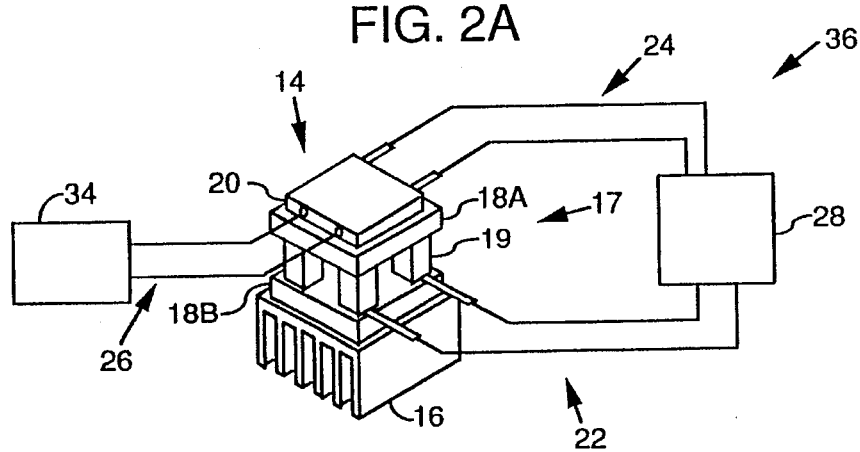
FIGS. 2A and 2B illustrate the humidity sensor of the present invention.
Figure 2B:
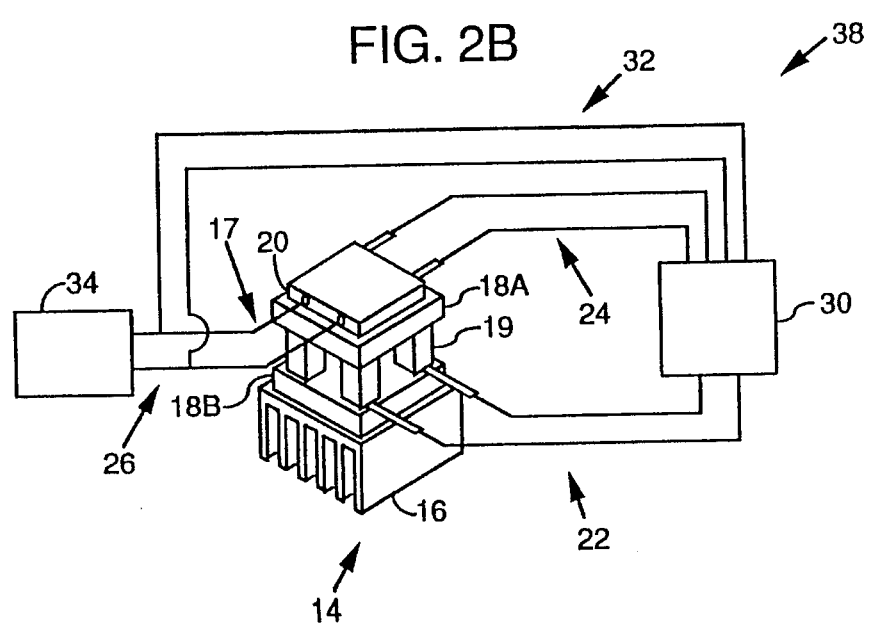
Figure 3:
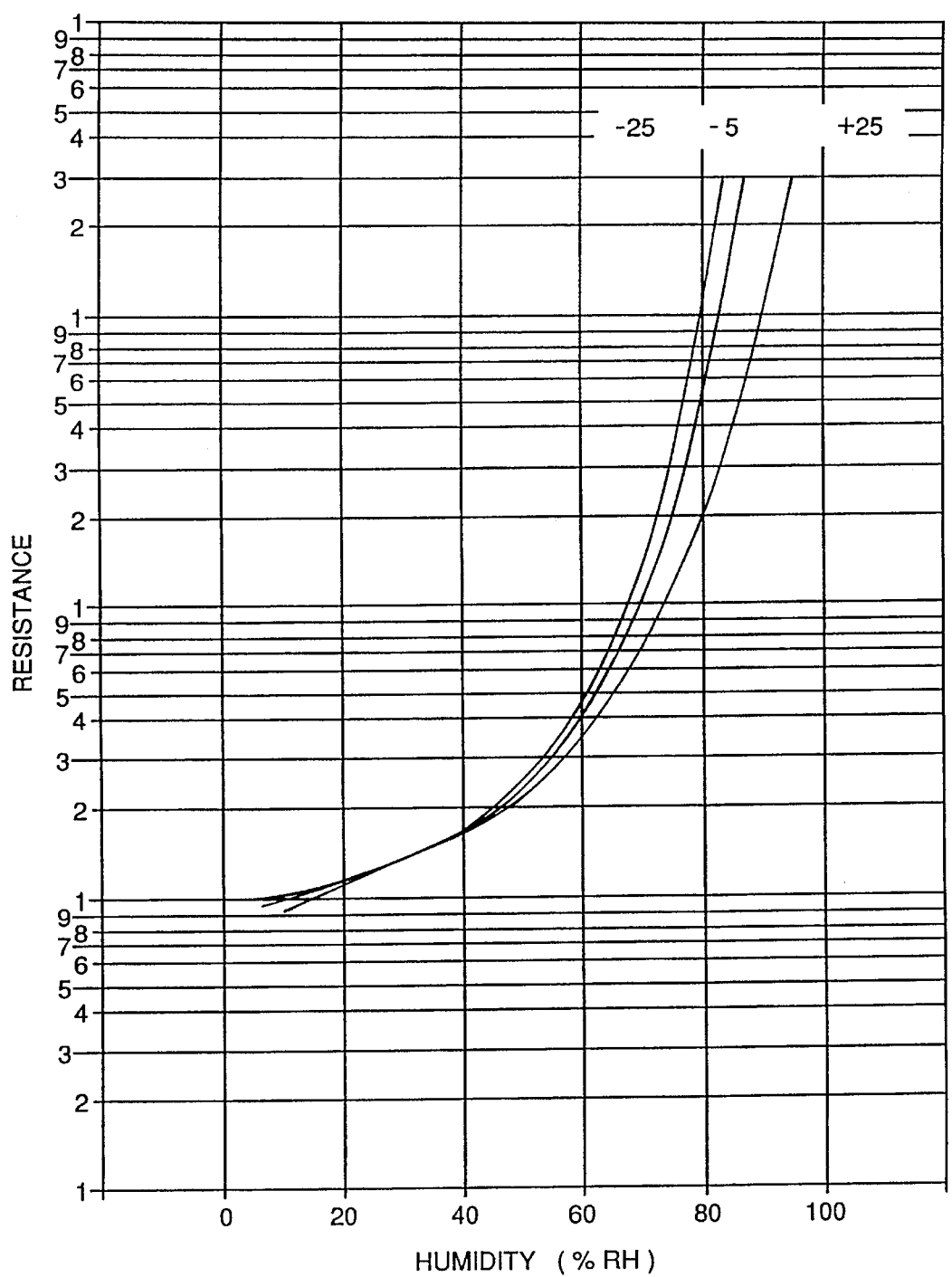
FIG. 3 is a graph of carbon element resistance versus relative humidity.
Figure 4:
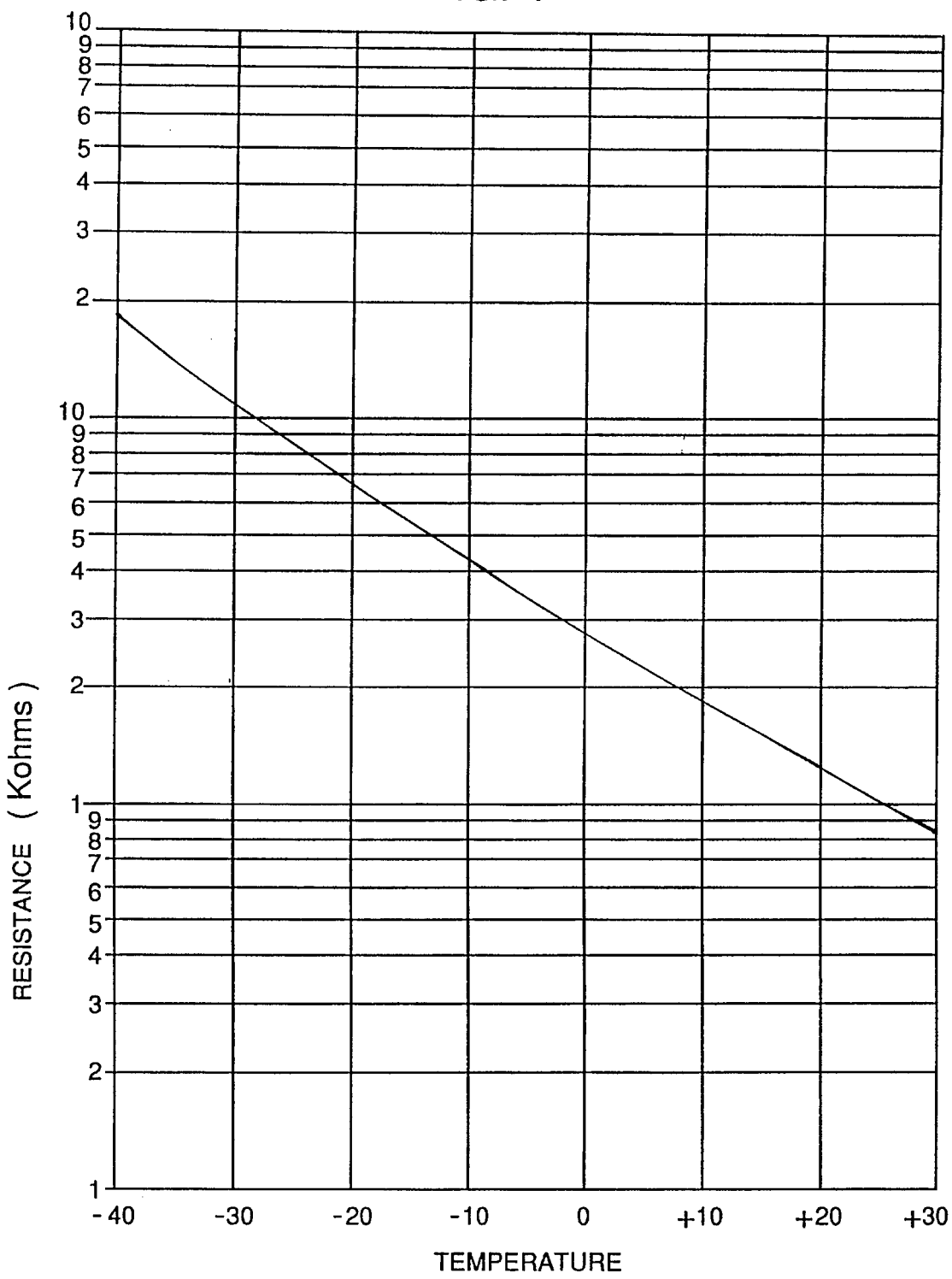
FIG. 4 is a graph of thermistor resistance versus temperature.
Figure 5:
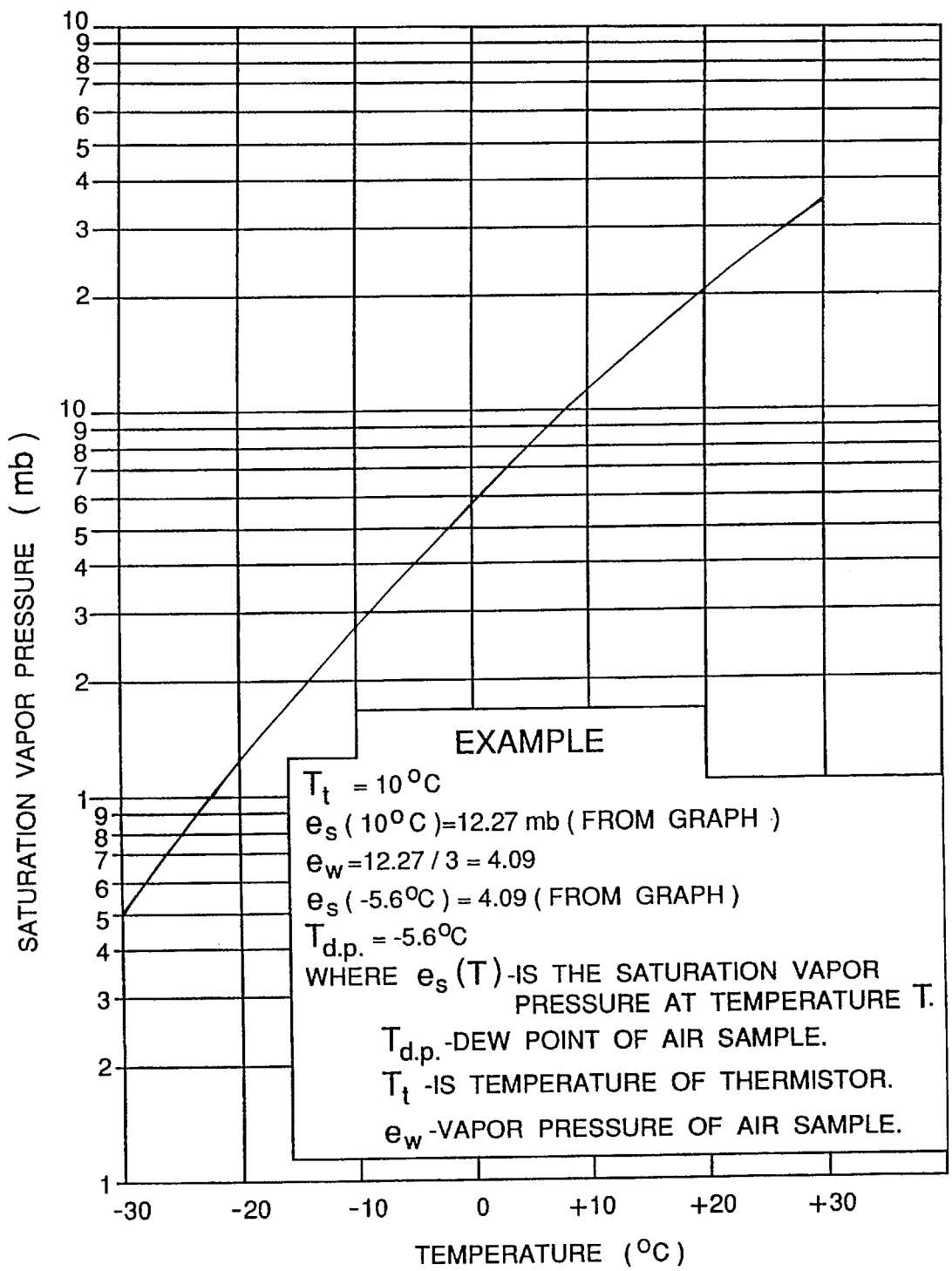
FIG. 5 is a graph of saturation vapor pressure versus temperature.

A new humidity sensing apparatus 36 and 38 are shown in FIGS. 2A and 2B, respectively. A humidity sensor 14 would be put in place of the carbon element 4 as shown in FIG. 1.

The humidity sensor 14 of the present invention is composed: a carbon element sensor 20 with a thermistor, not shown, either embedded, plated on, or otherwise attached thereto; a Peltier cooler 17 consisting of an upper and a lower plates 18A and 18B, respectively, and legs 19; and a heat sink 16. Control means 28 or 30 is connected to the Peltier cooler 17 and the carbon element sensor 20. The carbon element sensor leads 24 provide a resistance value to the control means 28 or 30. Thermistor leads 26 provide a resistance value to the output circuitry 34. A feedback circuit 32, FIG. 2B, may be used to provide temperature information to the control circuit 30 to allow for temperature compensation for some configurations to be discussed. With this compensation, constant relative humidity at the sensor 14 can be maintained at relative humidities other than 33% RH.

Two configurations of the invention, humidity sensing apparatus 36 or 38 are shown; apparatus 36, FIG. 2A, without a temperature feedback from the carbon element sensor 20 to the control means 28; and apparatus 38, FIG. 2B, with a temperature feedback 32 from the carbon element sensor 20 to the control means 30. This temperature feedback uses the resistance value of the thermistor embedded, plated on or otherwise attached to the carbon element sensor 20.

In general the control means 28 or 30 provides current to the Peltier cooler 17 in such a way as to heat up or cool down the carbon element sensor 20. This causes the air in contact with the element sensor surface to be heated or cooled which changes the relative humidity of the air. Heating decreases the relative humidity cooling increase the relative humidity. This change in relative humidity causes the resistance of the carbon element sensor 20 to change which is then fed into the control means 28 or 30.

Figure 6:
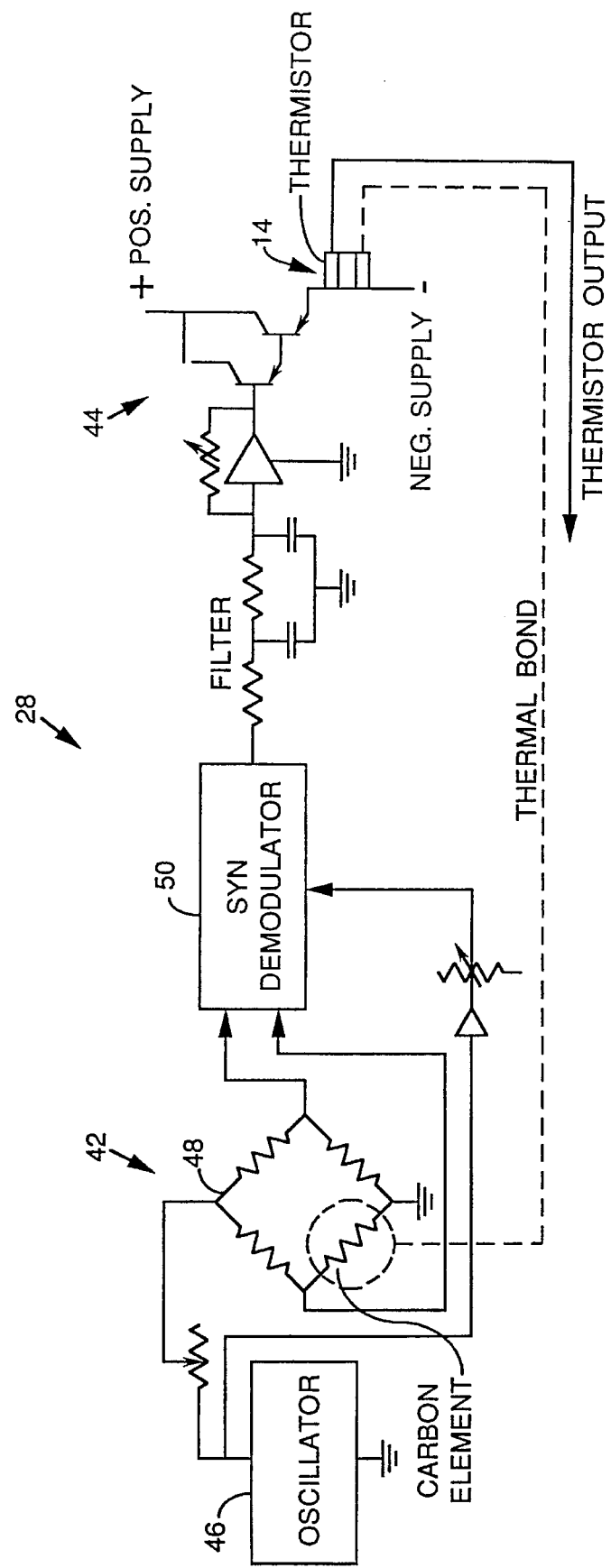
FIG. 6 is a circuit diagram of the control means.

In the simpler embodiment, FIG. 2A, the circuitry used in the control means 28 is designed to maintain a constant value of resistance at its input, which is the carbon element resistance. If this operating value is designed to be the resistance value the carbon element has at 33% RH, then the circuitry will maintain the humidity of the air in contact with the element constant when it keeps the resistance constant since the resistance is independent of temperature at 33% RH. The control means 28 is shown in FIG. 6. The control means 28 has an AC bridge circuit 42, and a DC amplifier-driver 44. The AC bridge 42 is composed of an oscillator 46, a resistance bridge 48, and a demodulator 50. The resistance of the carbon element is one arm of the bridge 48. The function of the AC bridge 48 is to generate a DC voltage which is proportional to any change in the resistance of the carbon element. A DC bridge could also be used for this purpose. The function of the DC amplifier-driver 44 is to take the DC voltage from the AC bridge 48 and amplify it to supply sufficient DC current and of the proper sense to the Peltier cooler 17 in the sensor to cause sufficient cooling or heating of the carbon element to return the resistance of the element to the desired value.

The temperature of the carbon element sensor 20 can be ascertained from the resistance of the embedded thermistor, see formula 1. This temperature can be used to determine water vapor pressure $e_w$ in (mb) by either looking it up in Smithsonian tables or by formulae 2 and 3.

$$T = \frac{1}{(1/T_o + 1/B \ln R(T)/R(T_o))} \quad (1)$$

where T is the temperature of the thermistor in °K.; $T_o$ is a temperature for which the resistance is known in advance. R(T) and R($T_o$) are the resistances of the thermistor at T and $T_o$ respectively; and B is a material constant for the material of the thermistor.

$$e_w = (RH) \times e_s \quad (2)$$

$$e_s = 6.1078e^{\frac{(17.56 T_c)}{(T_c + 241.9)}} \quad (3)$$

where $e_w$ is the ambient water vapor pressure in mb; $T_c$ is the temperature of the carbon element in degrees centigrade; $e_s$ is the saturation vapor pressure at $T_c$; and RH is the relative humidity expressed as a decimal. For this case RH would be 0.33 (33% RH).

Dew point temperature ($T_{dp}$) can then be ascertained using the value of $e_w$ and looking it up in the Smithsonian tables or by formula 4:

$$T_{dp} = \frac{241.9 (\ln e_w - 1.80957)}{19.37 - \ln e_w} \quad (4)$$

Using apparatus 36 and designing it to operate at 33% RH has other advantages. At 33% RH, the hysteresis is small and the sensitivity, % change in resistance per % change in RH, is still reasonably large. Also of importance is that the amount of cooling needed for low humidities is less than if the RH were maintained at a higher value than 33% RH.

The apparatus 36 can maintain a constant resistance at a value other than the value at 33% RH. This would result in the relative humidity at the sensor varying which is less desirable than the first embodiment. It requires an additional step in the data reduction. Once the temperature of the carbon element sensor 20 has been calculated from the resistance of the embedded thermistor, the relative humidity at the surface would have to be determined from the calibration of the sensor, see FIG. 7, or from a formula representing these calibrations. There are formulas currently in use for accomplishing this but it would depend on the manufacturer of the carbon element sensor 20. One such manufacturer is VIZ Manufacturing Co. and the formulas are shown in Tech. Publications #80415A and 80416A. Once this is accomplished the water vapor pressure can be obtained by formula 1 where $e_s$ would be ascertained as before using the $T_c$ and the RH would be the RH of the sensor determined as above. The dew point temperature could be evaluated using formula 4.

A third embodiment would be using the configuration in FIG. 2B which uses temperature compensation. This would allow the operation at constant relative humidity at points other than 33% RH. The control means would no longer be designed to maintain a constant resistance but would maintain the resistance according to the temperature of the element and the relative humidity that was being maintained.

Figure 8A:
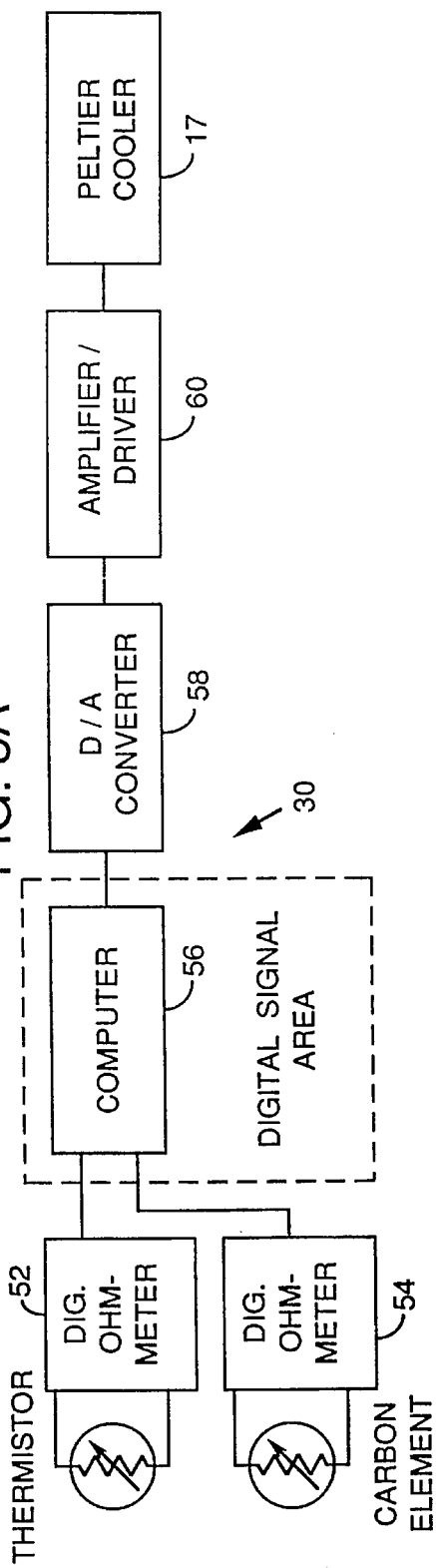
FIGS. 8A and 8B illustrate the control means wherein the operating point is at any desired relative humidity.
Figure 8B:
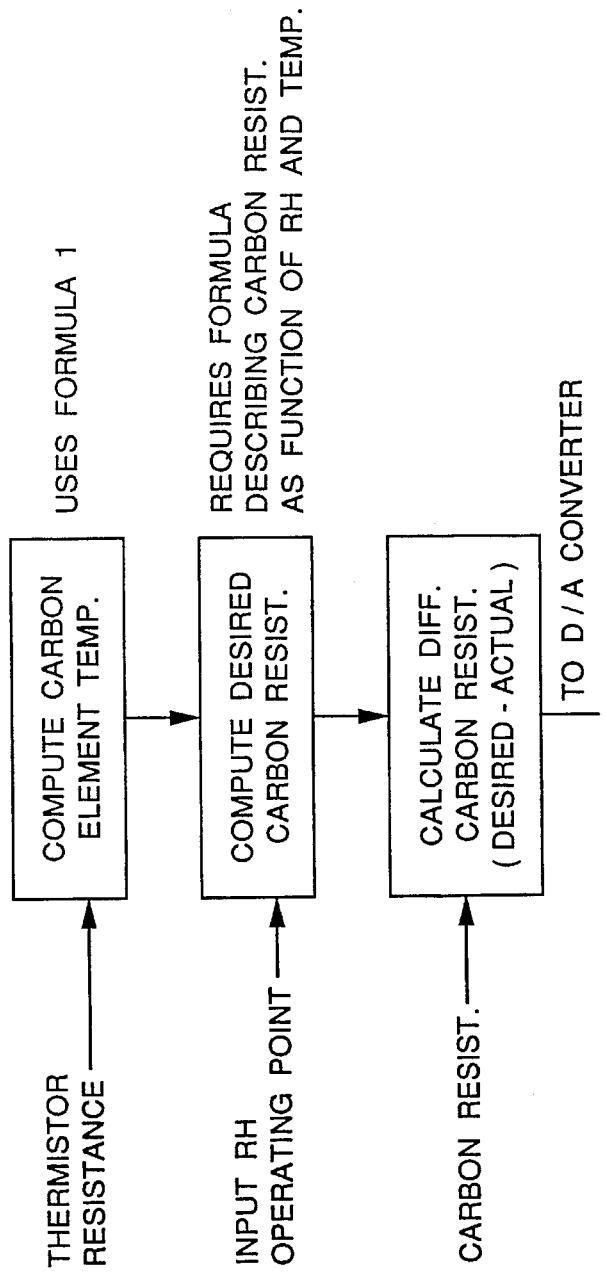

FIG. 8A is a block diagram of digital means for controlling the Peltier cooler 17. Digital ohmeters 52 and 54 would measure the resistance of the thermistor and the carbon element which would then be input into a computer 56; a digital-to-analog converter 58 and an amplifier-driver 60 process the output of computer 56 to adjust the current to the Peltier cooler 17. An output current would drive the Peltier cooler 17. FIG. 8B illustrates by flow diagram the general processing of information in the computer 56. Although digital processing techniques are shown, analog devices are possible.

Clearly, many modifications and variations of the present invention are possible in light of the above teachings and it is therefore understood, that within the inventive scope of the inventive concept, the invention may be practiced otherwise than specifically claimed.

What is claimed is:

1. A humidity sensing apparatus, said humidity sensing apparatus comprising:

a heat sink;

a Peltier cooler, said Peltier cooler having electrical leads for control current;

a relative humidity measuring sensor, said relative humidity measuring sensor having a changing resistance as a function of humidity, said relative humidity sensor being shielded from water thereon, said relative humidity measuring sensor mounted on top of said Peltier cooler opposite to the electrical leads from said Peltier cooler, said relative humidity measuring sensor having electrical leads for outputting resistance values;

a thermistor, said thermistor mounted in intimate contact to said relative humidity measuring sensor, said thermistor having a changing resistance as a function of temperature, said thermistor having output electrical leads for indicating resistance values therein;

control means, said control means for maintaining the resistance of said relative humidity measuring sensor at a predetermined value, said control means connected to said Peltier cooler and said relative humidity measuring sensor; and data collecting means, said data collecting means having input the leads from said thermistor to determine a resistance value thereof.

2. A humidity sensing apparatus as defined in claim 1 wherein said relative humidity measuring sensor is a carbon element sensor.

3. A humidity sensing apparatus as defined in claim 2 further including a feedback loop between said thermistor and said control means for making temperature compensation.

4. The humidity sensing apparatus of claim 2, wherein said relative humidity is selected in a range or from 25–40% RH such that the resistance of said carbon element sensor is about constant irrespective of the temperature.

5. A humidity sensor, said humidity sensor comprising:

a heat sink;

a Peltier cooler, said Peltier cooling having electrical leads for control current;

a relative humidity measuring sensor, said relative humidity measuring sensor being of a non-dew point type such that no water forms of said measuring sensor, said relative humidity measuring sensor having a changing resistance as a function of humidity, said relative humidity sensor being shielded from water, said relative humidity measuring sensor mounted on top of said Peltier cooler opposite to the electrical leads from said Peltier cooler, said relative humidity measuring sensor having electrical leads for outputting resistance values;

a thermistor, said thermistor mounted in intimate contact to said relative humidity measuring sensor, said thermistor having a changing resistance as a function of temperature, said thermistor having output electrical leads for indicating resistance values therein and control means for maintaining the resistance of said relative humidity measuring sensor at least one desired value in a range selected from the group consisting of 6–25% and 40–98% RH, where the RH is temperature dependent.

6. A process of measuring air characteristics, said process comprising the steps of:

protecting a relative humidity measuring sensor from water thereon;

maintaining a relative humidity on said relative humidity measuring sensor by adjusting a temperature of a Peltier cooler in direct contact with the relative humidity measuring sensor;

reading a resistance output of a thermistor in close contact with the relative humidity measuring sensor;

converting the resistance output to a temperature; and converting the temperature to a water vapor pressure.

7. A process as defined in claim 6 wherein the relative humidity measuring sensor is a carbon element sensor.

8. The process of claim 7 wherein the relative humidity is maintained in a range of from 25–40%.

9. A process as defined in claim 6 wherein said relative humidity is maintained on said sensor such that the relative humidity falls in the range selected from the group consisting of 6–25% and 40–98% wherein humidity is a function of temperature.

10. A process as defined in claim 9 including determining a water vapor pressure or a dew point temperature.

* * * * *